United States Patent
Zeller

(10) Patent No.: US 11,340,326 B2
(45) Date of Patent: May 24, 2022

(54) CORRECTION OF MR OBJECT MOVEMENTS

(71) Applicant: Siemens Healthcare GmbH, Erlangen (DE)

(72) Inventor: Mario Zeller, Erlangen (DE)

(73) Assignee: Siemens Healthcare GmbH, Erlangen (DE)

( * ) Notice: Subject to any disclaimer, the term of this patent is extended or adjusted under 35 U.S.C. 154(b) by 2 days.

(21) Appl. No.: 16/917,132

(22) Filed: Jun. 30, 2020

(65) Prior Publication Data

US 2021/0003652 A1    Jan. 7, 2021

(30) Foreign Application Priority Data

Jul. 1, 2019    (DE) .......................... 102019209604.2

(51) Int. Cl.
| | |
|---|---|
| *G01R 33/561* | (2006.01) |
| *G01R 33/48* | (2006.01) |
| *A61B 5/055* | (2006.01) |
| *G01R 33/56* | (2006.01) |

(52) U.S. Cl.
CPC .......... *G01R 33/5615* (2013.01); *A61B 5/055* (2013.01); *G01R 33/4822* (2013.01); *G01R 33/5608* (2013.01); *G01R 33/5611* (2013.01)

(58) Field of Classification Search
CPC ............ G01R 33/4822; G01R 33/5608; G01R 33/5611; G01R 33/5615; A61B 5/055
See application file for complete search history.

(56) References Cited

U.S. PATENT DOCUMENTS

| | | | | |
|---|---|---|---|---|
| 2006/0261810 | A1* | 11/2006 | Fautz | G01R 33/56375 324/309 |
| 2008/0310696 | A1* | 12/2008 | Hwang | G01R 33/56341 382/131 |
| 2012/0002858 | A1 | 1/2012 | Huang | |
| 2015/0198683 | A1* | 7/2015 | Takeshima | G01R 33/4818 324/318 |
| 2018/0095143 | A1 | 4/2018 | Zeller | |
| 2020/0096588 | A1 | 3/2020 | Vester | |

FOREIGN PATENT DOCUMENTS

| | | |
|---|---|---|
| DE | 102016219052 B3 | 3/2018 |
| DE | 102018216362 B3 | 12/2019 |

OTHER PUBLICATIONS

Blaimer, Martin, et al. "SMASH, SENSE, PILS, GRAPPA: how to choose the optimal method." Topics in Magnetic Resonance Imaging 15.4 (2004): 223-236.

(Continued)

*Primary Examiner* — Gregory H Curran
(74) *Attorney, Agent, or Firm* — Lempia Summerfield Katz LLC

(57) ABSTRACT

A method for correcting magnetic resonance (MR) object movements includes performing a recording of an MR object with multiple echo trains. k-space data pertaining to an echo train regarded as impaired by an MR object movement is corrected by linking the k-space data to corresponding k-space data reconstructed from k-space data of other echo trains by a PPA method.

11 Claims, 3 Drawing Sheets

(56) References Cited

OTHER PUBLICATIONS

Bydder, Mark, David J. Larkman, and Joseph V. Hajnal. "Detection and elimination of motion artifacts by regeneration of k-space." Magnetic Resonance in Medicine: An Official Journal of the International Society for Magnetic Resonance in Medicine 47.4 (2002): 677-686.
German Office Action for German Application No. 10 2019 209 604.2 dated May 8, 2020.
Griswold, Mark A., et al. "Generalized autocalibrating partially parallel acquisitions (GRAPPA)." Magnetic Resonance in Medicine: An Official Journal of the International Society for Magnetic Resonance in Medicine 47.6 (2002): 1202-1210.
Lin, Wei, et al. "Motion correction using an enhanced floating navigator and GRAPPA operations." Magnetic Resonance in Medicine: An Official Journal of the International Society for Magnetic Resonance in Medicine 63.2 (2010): 339-348.
Ma, Jingfei. "Dixon techniques for water and fat imaging." Journal of Magnetic Resonance Imaging: An Official Journal of the International Society for Magnetic Resonance in Medicine 28.3 (2008): 543-558.
Moeller, S., et al. "Unaliasing of multiband multislice EPI and GRE imaging with GRAPPA." Proc Intl Soc Magn Reson Med. vol. 17. 2009. pp. 1544.
Warntjes, J. B. M., et al. "Rapid magnetic resonance quantification on the brain: optimization for clinical usage." Magnetic Resonance in Medicine: An Official Journal of the International Society for Magnetic Resonance in Medicine 60.2 (2008): 320-329.
Zhang, Tao, et al. "Coil compression for accelerated imaging with Cartesian sampling." Magnetic resonance in medicine 69.2 (2013): 571-582.

* cited by examiner

CORRECTION OF MR OBJECT MOVEMENTS

This application claims the benefit of DE 10 2019 209 604.2, filed on Jul. 1, 2019, which is hereby incorporated by reference in its entirety.

BACKGROUND

The present embodiments relate to the correction of magnetic resonance (MR) object movements.

The identification and correction of object movements during and between magnetic resonance tomography (MRT) imaging sequences is a major challenge in MR imaging. Depending on the imaging sequence, the movement of an object may restrict the diagnosis or make diagnosis completely impossible. A new, correspondingly more time-consuming recording may accordingly become necessary.

For example, during a turbo spin echo (TSE) recording (e.g., fast spin echo (FSE) or rapid acquisition with refocused echoes (RARE)), the k-space is recorded successively in multiple spin echo trains or echo trains (e.g., in the form of multiple rows in the k-space that correspond to different phase encoding steps). An echo train consists of an MR excitation pulse followed by multiple refocusing pulses, between which in each case a k-space row is read out based on a spin echo generated by the preceding refocusing pulse. The time interval between two consecutive echo trains is typically in the range of several seconds, while the recording duration of an echo train is generally only a few tens of milliseconds to a few hundred milliseconds. In a variant, the echo trains may be initiated by triggering. The effect of a patient movement (e.g., of an erroneous triggering caused thereby) on the reconstructed MR image results in an offset in the readout position or a phase offset, which results in numerous ghosting artifacts compared to an MR image without patient movement.

A multiplicity of methods exists to solve this problem. These include correction methods based on sequence-inherent navigators, external sensors such as cameras, "field probes", "pilot tone" recordings, or retrospective methods. Methods also exist in which recordings are only performed in specific respiratory or EKG states. In this case, the recording or trigger time points are established by navigators or external sensors. However, if an erroneous detection of a trigger time point occurs or if an additional object movement occurs after the trigger is initiated, the result is a reduction in image quality.

Partially parallel acquisition (PPA) is known for particularly fast generation of an MR image, in which in comparison to a complete acquisition of echoes or associated k-space rows or phase encoding rows or lines, these are only partially acquired. PPA methods use spatial information that is contained in component coils of a coil array of an MR device in order partially to replace the spatial encoding that is normally performed using gradients. As a result of this, the recording or imaging time is reduced. A specialized reconstruction is then applied to the recorded or acquired k-space data in order to reconstruct the missing (not acquired) k-space data, which in a fraction of the otherwise normal time, results in a complete MR image in the predefined spatial range (field of view (FOV)). PPA methods are often also called "parallel imaging" methods or "parallel MRI" (pMRI).

For example, in Mark A. Griswold et al.: "Generalized Autocalibrating Partially Parallel Acquisitions (GRAPPA)," Magn Reson Med, vol. 47, pp. 1202-1210 (2002), an embodiment of a PPA method using a GRAPPA method is described. Other PPA methods such as SMASH, SENSE, or PILS are described in the overview article by M. Blaimer et al: "SMASH, SENSE, PILS, GRAPPA—How to Choose the Optimal Method," Top Magn Reson Imaging, vol. 15, pp. 223-236 (2004) in addition to GRAPPA.

SUMMARY AND DESCRIPTION

The scope of the present invention is defined solely by the appended claims and is not affected to any degree by the statements within this summary.

The present embodiments may obviate one or more of the drawbacks or limitations in the related art. For example, an improved retrospective movement correction for MR imaging, specifically for triggered recordings, is provided. For example, a robust movement correction for triggered MR recordings is provided.

A method includes performing an MR recording of an MR object with multiple echo trains. The method also includes correcting k-space data pertaining to an echo train impaired by an MR object movement by being linked to corresponding k-space data reconstructed by a PPA method at least from k-space data of other echo trains.

The advantage that a movement correction for the MR imaging is provided in a particularly reliable and robust manner, enabling a reduction in movement artifacts in MR images, is provided. Consequently, an increase in image quality and thus an improved prevention of erroneous diagnoses are provided.

This method uses the idea of correcting regions (e.g., rows) of the k-space that are impaired or "corrupted" by a movement of an object (e.g., "MR object"; a living object such as a human patient or an animal) examined during such an MR recording, with the aid of methods known from partially parallel acquisition (PPA). This type of correction is a retrospective correction (e.g., a correction that corrects k-space data after the k-space data has been recorded, or retroactively). In this instance, the reconstruction is therefore not used to generate missing k-space data, but to correct measured but possibly movement-impaired k-space data using reconstructed k-space data.

Which k-space data is impaired by an MR object movement may be established or be known prior to the correction (e.g., by external sensors), not established until during the correction, and/or simply assumed or stipulated. It may also happen that none of the k-space data is movement-impaired, where the method may then, for example, be paused or nevertheless applied.

The linking of k-space data pertaining to an impaired echo train to corresponding k-space data reconstructed "at least" from k-space data of other echo trains may include linking the k-space data pertaining to the impaired echo train only to k-space data of other echo trains (e.g., only to k-space data of other unimpaired echo trains). Alternatively or additionally, the k-space data pertaining to the impaired echo train may additionally be linked to k-space data of the impaired echo train itself. Although impaired k-space data is also included in the correction, in this case, a negative impact on the correction is usually minor, since the impaired k-space data generally only forms a subset of all k-space data used for the correction.

In general, the k-space data pertaining to one or more echo trains that are impaired or assumed to be impaired may be corrected.

In one embodiment, the MR recording is a TSE recording. In the TSE recording, multiple TSE sequences or "echo trains" are generated consecutively, where each echo of an echo train contains a different phase encoding and typically fills one row in the k-space. TSE recordings are known and are not explained in more detail below.

However, the MR recording does not need to be a TSE recording. Rather, the method may be performed using segmented methods. For example, the method may be used as an alternative to a TSE recording in echo planar imaging (EPI).

In one embodiment, the reconstructed k-space data is generated by a GRAPPA method (e.g., in accordance with a method described in Mark A. Griswold et al.). Impaired k-space rows (e.g., corresponding to the k-space data from echoes of an echo train to be regarded as impaired) may, for example, be reconstructed or synthesized from data of adjacent k-space rows (e.g., corresponding to the k-space data from echoes of a non-impaired echo train). By correcting the k-space rows of an impaired echo train, ghosting artifacts are reduced or eliminated. The use of the GRAPPA method enables fast and high-quality reconstruction of k-space values. A further advantage is that in this way the correction of movement-impaired k-space data may be combined particularly easily with partially parallel imaging methods (e.g., the GRAPPA method).

To use the GRAPPA method, optionally used calibration data may be obtained directly from the recorded k-space (e.g., by using "sliding window" methods). In this case, the impaired k-space rows may be included in the calibration. Since combinations with the impaired k-space rows, however, only form a subset of all calibration combinations, the negative impact of the subset on the calibration of the GRAPPA kernel is minor. Alternatively, the calibration data may be determined from a brief prescan.

Compared to conventional partially parallel imaging with GRAPPA, in which a regular undersampling of the k-space takes place, which is disadvantageously accompanied by a signal to noise (SNR) reduction by the factor $R^{1/2}$, where R is the so-called GRAPPA factor, the SNR reduction in the present method is generally very minor. This is due to usually only a fraction of the k-space rows being actually replaced and not, as in the PPA method according to GRAPPA, a number $(R-1)/R$ of k-space rows.

The echo trains or MR sequences are, for example, echo trains or MR sequences initiated by triggering.

In one embodiment, the reconstructed k-space points are generated by a 3×4 GRAPPA kernel. This produces a reliable reconstruction with short computing times. In a 3×4 GRAPPA kernel, a k-space point $(k_i, k_j)$ of a k-space row $\{k_x\}|_{ky=const}$ may, for example, be reconstructed taking into consideration twelve adjacent k-space points out of three k-space points from in each case four other k-space rows:
$(k_{i-1},k_{j+2})$, $(k_i,k_{j+2})$, $(k_{i+1},k_{j+2})$;
$(k_{i-1},k_{j+1})$, $(k_i,k_{j+1})$, $(k_{i+1},k_{j+1})$;
$(k_{i-1},k_{j-1})$, $(k_i,k_{j-1})$, $(k_{i+1},k_{j-1})$;
$(k_{i-1},k_{j-2})$, $(k_i,k_{j-2})$, $(k_{i+1},k_{j-2})$.

When using a 3×4 GRAPPA kernel, an MR recording is to include at least five individual echo trains or MR sequences with at least three echoes in each case. The k-space data of an impaired echo train is not itself included in the reconstruction. However, the embodiment is not restricted to a 3×4 GRAPPA kernel, and other kernel dimensions may also be used (e.g., 4×5, 2×7, etc.).

In one development, the corrected k-space data or values thereof may depend both on the reconstructed k-space data and also on the corresponding (e.g., pertaining to the same k-space points) impaired k-space data. This produces the potential advantage that the impaired k-space data may be taken into consideration when determining the corrected k-space data. The link may be performed, for example, by a formula, based on which the corrected k-space data is determined, by using elementary algebra, from the values of corresponding reconstructed and original, impaired k-space points. For example, a corrected k-space point may be calculated as a weighted average value from the corresponding reconstructed and impaired k-space points.

In one embodiment, the linking includes replacing the k-space data pertaining to an impaired echo train by corresponding reconstructed k-space data. The corrected k-space data thus corresponds to the reconstructed k-space data. This produces the potential advantage that the impaired k-space data is not included in the values of the corrected k-space data.

In one embodiment, at least one echo train is identified as movement-impaired prior to the performance of the correction and is thus known prior to the performance of the correction. An identification may, for example, be performed by external hardware (e.g., a camera, a pilot tone method, or a respiratory sensor) or sequence-inherent navigators. For example, by comparing respiratory curves at the recording time point of the respective echo trains, the time points at which a respiratory curve has shown a strong deviation (e.g., in shape or amplitude) may be determined. The k-space data (e.g., k-space rows) of the identified echo trains is then corrected by the present method.

Alternatively or additionally, an identification for movement-impaired k-space data takes place by comparing whether the correction of the k-space data improves the MR image.

In one development, the k-space data of an echo train is reconstructed. The corresponding original k-space data of this echo train is corrected by the reconstructed k-space data. A size of a deviation of the corrected k-space data of the echo train from the corresponding original k-space data is determined, and if the size of the deviation exceeds a predefined amount, the corrected k-space data is retained; otherwise, the original k-space data is retained.

Thus the advantage is achieved that movement-impaired echo trains are recognized or identified from the recorded k-space data itself, and separate identification devices or acts, such as external hardware, etc., may be dispensed with. This embodiment may be repeated for all echo trains. It is also alternatively possible to apply a plausibility check for movement impairment to movement-impaired k-space data identified by separate identification devices or acts thanks to this embodiment.

To determine whether the size of the deviation may exceed a predefined amount, a threshold value of a percentage deviation of the k-space amplitude(s) of the original k-space data from the reconstructed k-space data may, for example, be used as a criterion. If the deviation is minor and thus lies below the threshold value, it may be assumed that no significant object movement has taken place. Alternatively, a comparison of a phase smoothness between adjacent k-space rows may also be used. A known algorithm for evaluating similarity (e.g., "mutual information") may be employed. The comparison of the k-space data as such has the advantage of high speed, since a complete image does not need to be reconstructed for this. Alternatively, an image-space-based evaluation is possible.

In the event that the correction includes a simple replacement of the original k-space data by the corresponding reconstructed k-space data, in one development. The k-space data of an echo train is reconstructed. A size of a deviation of the reconstructed k-space data of the echo train from the corresponding original k-space data is determined. If the size of the deviation exceeds a predefined amount, the original k-space data is replaced by the corresponding reconstructed k-space data; otherwise, the original k-space data is retained.

In one embodiment: (i) the k-space data of precisely one echo train is reconstructed from a k-space of all measured k-space data; and a corrected k-space, which contains k-space data present after act (i), is stored. The acts (i) and (ii) are performed afresh for each echo train. An MR image is constructed from the corrected k-spaces.

Thus, the advantage is achieved that even in the absence of identification of movement-impaired echo trains an artifact-reduced MR image may be generated by using PPA methods.

In act (i), therefore, only the k-space data (e.g., k-space rows) of a particular echo train from a k-space that contains all recorded k-space data (e.g., k-space rows) is corrected (e.g., replaced) by a PPA method. For example, a separate "corrected" k-space is created for each echo train, in which the k-space rows pertaining to the echo train are replaced by k-space rows obtained, for example, from the adjacent rows by partially parallel imaging, but all other k-space rows are retained. Alternatively, the k-space rows pertaining to an echo train to be corrected are not completely replaced by the reconstructed k-space rows, but are algebraically linked thereto (e.g., added in a weighted manner).

In act (ii), the "corrected" k-space image generated by the correction of the one echo train is saved.

Acts (i) and (ii) are repeated at least for some (e.g., for all) echo trains.

In one embodiment, associated individual ("corrected") MR images are generated from the k-space data of respective corrected k-spaces in act (ii), and a final MR image is generated from the corrected MR images in act (iv). Thus, the advantage of a particularly simple implementation is achieved. In other words, this embodiment entails generating a corrected MR image for each of the corrected k-spaces. A final artifact-reduced image is then obtained from the corrected MR images through an appropriate combination.

In one embodiment, the final MR image is generated using one or more of the following methods in act (iv): pixel-by-pixel average value formation of multiple (e.g., all) corrected MR images; use of a mask that masks out the anatomy from the corrected MR images; and selection of the corrected MR image which has the least artifact energy in external regions. As a result, the corrected MR image with the least ghosting intensity is selected as the final MR image. Additional methods that may be used in act (iv) include pixel-by-pixel selection of the image content with the least intensity. By this comparatively simple implementation alone, ghosting artifacts may be significantly reduced compared to an original recording that exhibits erroneous triggering. A so-called "low-rank" approximation and/or a "singular value decomposition" along the dimension of the corrected MR images may be used. Alternatively or additionally, a "machine learning" or "deep learning" method may be used for identification of the optimum reconstruction.

The use of a mask is generally known and may be performed automatically. External regions may be regions of the MR image that are identified during the masking as being located outside the body. A ghosting intensity may correspond to an energy or intensity in the external regions. If no artifacts occur, there should be only slight noise here. A least artifact energy may be determined, for example, via a brightness of pixels. A least ghosting intensity may be a least cumulated brightness of the pixels in the external regions. A weighted averaging may, however, be used, whereby greater attention is given to regions further out or in which no fold artifacts due to parallel imaging methods are to be expected.

For "low rank" approximation, see, for example, Tao Zhang, "Coil Compression for Accelerated Imaging with Cartesian Sampling," Magn Reson Med. 2013, February; Vol. 69(2), pages 571-582.

In general, the method described above may also be applied iteratively by optimizing the MR image by adding or removing corrected echo trains. This may, for example, be implemented such that an MR image is created from a first set of original and corrected echo train k-space data and is evaluated. A second image with a changed composition of the original and corrected echo train k-space data are then created and evaluated. If the evaluation of the second image is better, the first set is rejected, and the second set of k-space data is used; if the second image is worse, then vice versa. This is repeated with different combinations, until the evaluation scarcely changes.

In addition, instead of correcting all k-space data (e.g., k-space lines) of an echo train regarded as movement-impaired, a correction for each individual spin echo or each individual k-space line may take place in the most accurate but also most compute-intensive case. This provides that the k-space data of each spin echo or of each k-space line may be checked individually for a movement impairment and, if necessary, corrected. Since the recording duration of an echo train generally lasts only a few tens of milliseconds up to a few hundred milliseconds and, in the case of a triggered recording, is triggered for each echo train, the correction of all k-space data of an echo train regarded as movement-impaired is, however, generally advantageous.

Advantageously, the method may be employed for multi-echo or Dixon recordings, see, e.g., J. B. M. Warntjes et al.: "Rapid Magnetic Resonance Quantification on the Brain: Optimization for Clinical Usage," Magnetic Resonance in Medicine, Vol. 60, pages 320-329, (2008) and Jingfei Ma: "Dixon Techniques for Water and Fat Imaging," JOURNAL OF MAGNETIC RESONANCE IMAGING, Vol. 28, pages 543-558 (2008). Here, each k-space row is present for each recorded contrast, such that by including the data of the other contrasts, a particularly accurate detection or reconstruction of the k-space lines is possible. See, e.g., DE 10 2016 219 052 B3, in which it is disclosed that the k-space rows of other contrasts may be used in the determination of the GRAPPA kernels. In the evaluation of the movement detection described above, a comparison of k-space rows or image data may additionally take place with the corresponding pendants from the other contrast. If the similarity is high, this argues against an appreciable MR object movement.

The method may be expanded such that k-space data (e.g., of a particular echo train or a particular MR sequence) identified as or assumed to be movement-impaired may be recorded afresh if a predefined condition or a predefined scenario is satisfied. This has the advantage of fewer SNR losses, and an acceptable image quality may be achieved even if a plurality of echo trains is affected. Thus, for example, a fresh recording may take place if a particular number or a particular proportion of echo trains is classified as movement-impaired. A fresh recording may also take place if primarily a center of the k-space is movement-impaired, and may be dispensed with if primarily a k-space periphery is affected by the movement impairment.

As another example, a data processing device that is configured to carry out the method as described above is provided. The data processing device may be embodied in an analogous manner to the method and produces the same advantages. The data processing device may include one or more processors.

The data processing device may be a concrete and/or functional component of an MR system.

As yet another example, a computer program product including commands that when the program is executed by a data processing device prompt the data processing device to carry out the method as described above is provided.

As another example, a computer-readable storage medium (e.g., a non-transitory computer readable storage medium) that stores commands (e.g., instructions) that when executed by a computer or a data processing device (e.g., one or more processors) prompt the computer or the data processing device to carry out the method as described above is provided.

BRIEF DESCRIPTION OF THE DRAWINGS

The above-described characteristics, features and advantages of this invention, as well as the manner in which these are realized, will become more clearly and easily intelligible in connection with the following schematic description of exemplary embodiments, which are explained in more detail with reference to the drawings. For clarity of illustration, identical elements, or elements having an identical effect, may be given identical reference characters.

DETAILED DESCRIPTION

Figure 1:
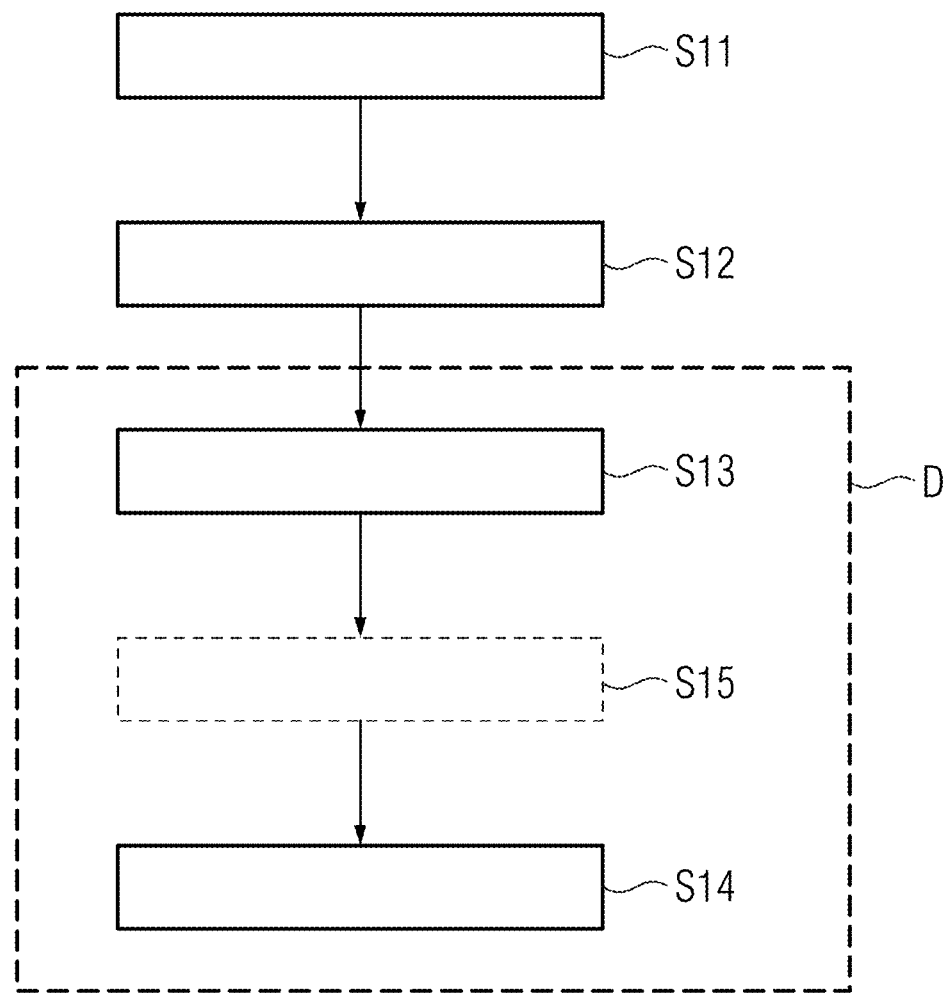
FIG. 1 shows a flow diagram of a first exemplary embodiment of a method.

FIG. 1 shows a flow diagram of a first embodiment of a method.

The flow diagram includes a first act S11, in which a turbo spin echo (TSE) recording of a magnetic resonance (MR) object with multiple TSE sequences or echo trains is performed.

In a second act S12, information about which echo train(s), if any, is movement-impaired is received. As a result, at least one movement-impaired echo train may be identified prior to the performance of the correction. The information may, for example, be obtained by external hardware (e.g., a camera, a pilot tone method, or a respiratory sensor) or sequence-inherent navigators.

In a third act S13, k-space rows pertaining to movement-impaired echo trains are replaced by k-space rows reconstructed by a GRAPPA method. The remaining, non-movement-impaired k-space rows are retained without change.

In act S14, an MR image may be generated from the k-space resulting from act S13.

After act S13, it is possible to check in an optional act S15 whether the MR image is improved by the replacement of the k-space rows classified as movement-impaired. This may be implemented, for example, in that a size of a deviation of the corrected k-space rows from the corresponding uncorrected k-space rows is determined. If the size of the deviation exceeds a predefined amount, the uncorrected k-space rows of the echo train classified as movement-impaired are replaced by the corresponding corrected k-space rows, or the replacement is retained. Otherwise, the uncorrected k-space rows are retained, or the replacement is reversed by the corresponding corrected k-space rows.

At least the acts S13 to S15 may be carried out by a correspondingly set up (e.g., programmed) data processing device D. The data processing device D may represent a part of an MR system, by which the acts S11 and S12 may also be carried out.

Figure 2:
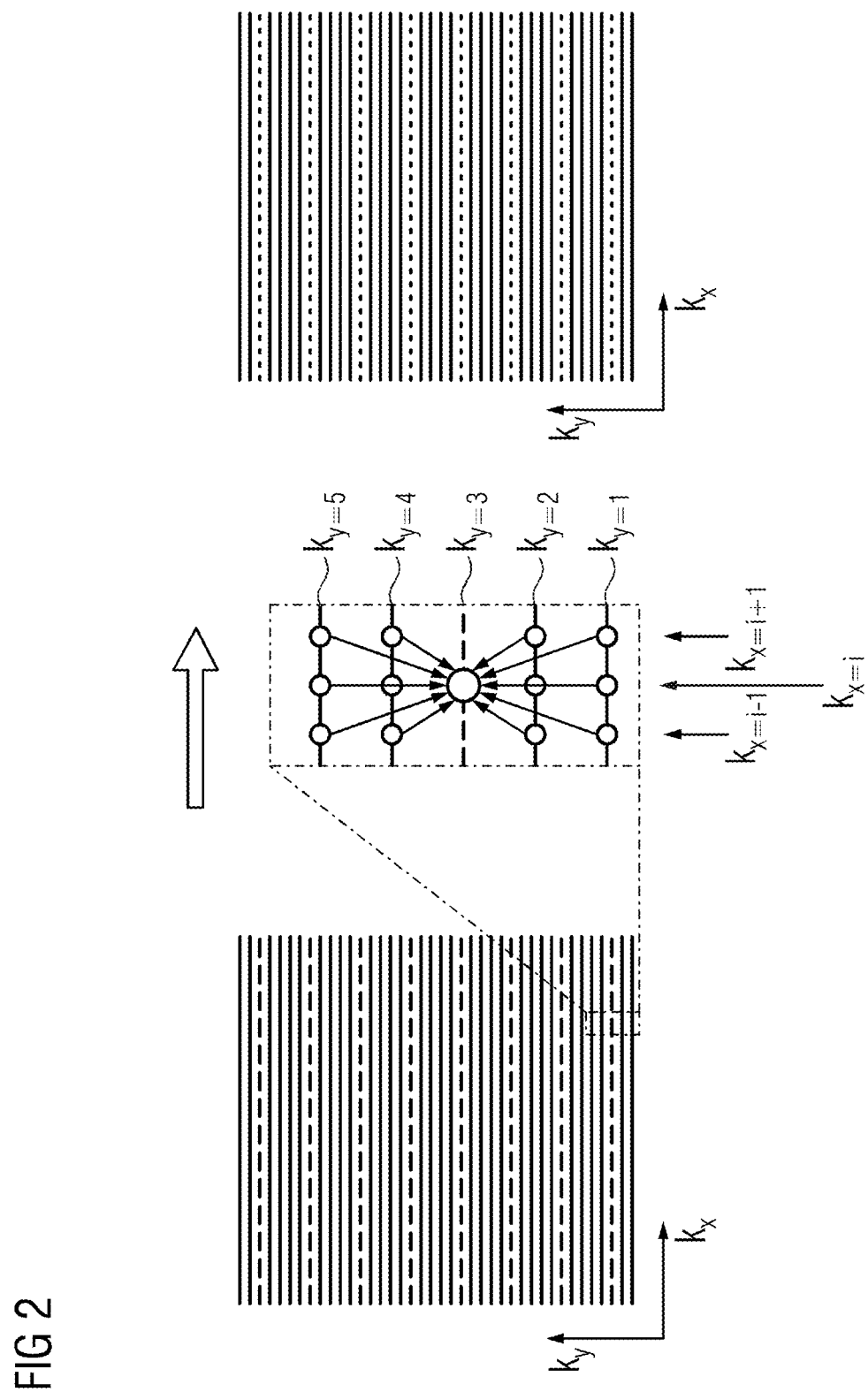
FIG. 2 shows a sketch of a variant of the first exemplary embodiment with a 3×4 GRAPPA kernel.

FIG. 2 shows a sketch of a variant of the first exemplary embodiment, in which reconstructed k-space points of a k-space row are generated by a 3×4 GRAPPA kernel. In this case, an original, uncorrected two-dimensional k-space or portion thereof is represented on the left-hand side, while on the right-hand side, a GRAPPA-corrected two-dimensional k-space or portion thereof is represented. The coil dimension $k_z$ is not represented but is optionally present. A 3×4 GRAPPA kernel applied to the uncorrected k-space is indicated in enlarged form between the two k-spaces.

The k-spaces have k-space rows $\{k_x\}|_{ky=const.}$ that each represent spin echoes of an echo train. The k-space rows of the spin echoes of an identical echo train are arranged spaced evenly apart in the ky direction and are represented separately from k-space rows of the spin echoes of other echo trains. A TSE recording with five echo trains with eight spin echoes in each case is represented in this case by a k-space purely by way of example. The third echo train (drawn in dashed form) is assumed to be or is classified as movement-impaired here.

Each k-space row has multiple k-space points $(k_i, k_j)$ distributed along a $k_x$ axis, where i=[1, . . . , xmax] and j=y=const.

By the 3×4 GRAPPA kernel, the k-space points of the k-space rows of the movement-impaired third echo train (drawn in dashed form in the left-hand k-space) are reconstructed from k-space points of the k-space rows adjacent thereto of the first, second, fourth, and fifth echo trains and are then replaced by the reconstructed k-space points (drawn with dotted lines in the right-hand k-space). By way of example, $k_1$ here designates the first k-space row of the first echo train, $k_2$ designates the first k-space row of the second echo train, . . . , $k_6$ designates the second k-space row of the first echo train, etc. In this case, the 3×4 GRAPPA kernel is applied to the first k-space rows of the five echo trains such that an i-th point $(k_i, k_3)$ of the first k-space row $k_3$ of the movement-impaired third echo train is reconstructed in each case by three points $(k_{i-1}, k_m)$, $(k_i, k_m)$, $(k_{i+1}, k_m)$ of the four k-space rows $k_m$, where m=1, 2, 4 and 5.

The 3×4 GRAPPA kernel is shifted by one place from i to the right for the reconstruction of the (i+1)-th point $(k_i, k_3)$ of the first k-space row $k_3$.

Figure 3:
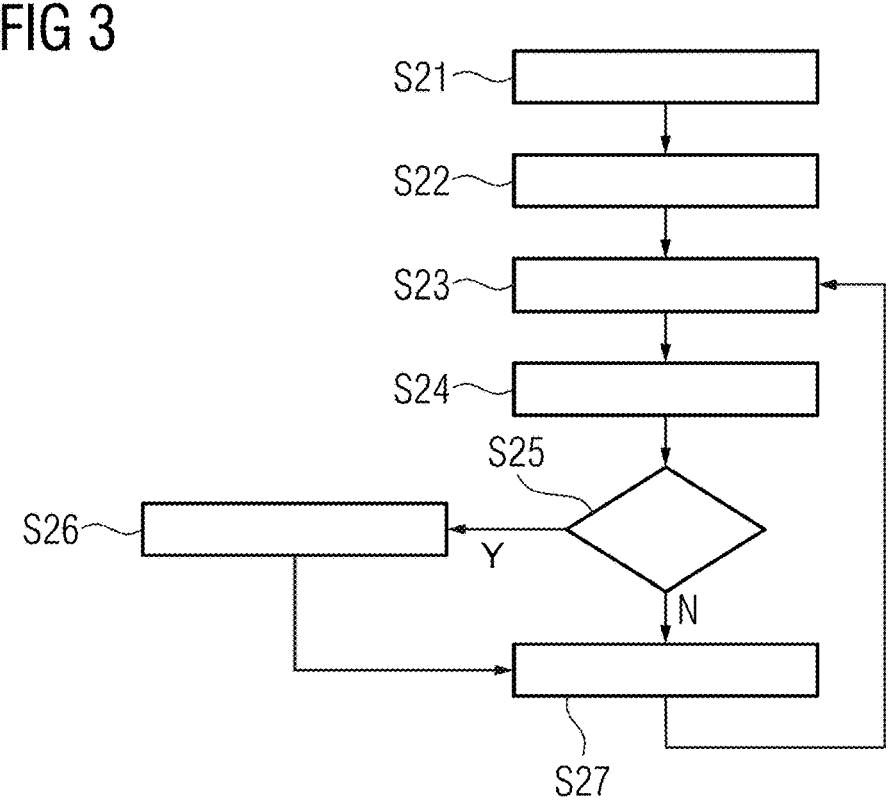
FIG. 3 shows a flow diagram of a second exemplary embodiment of the method.

FIG. 3 shows a flow diagram of a second exemplary embodiment of the method.

In a first act S21, a TSE recording of an MR object with multiple TSE sequences or echo trains is performed.

In a second act S22, a particular "first" echo train of the k-space is selected.

In a third act S23, k-space rows reconstructed by GRAPPA are generated for k-space rows pertaining to this echo train. In a variant, these may then be linked to the corresponding original k-space rows in order to generate corrected k-space rows.

In a fourth act S24, the corrected k-space rows are compared with the originally recorded k-space rows. For example, a size of a deviation of the corrected k-space rows from the originally recorded, uncorrected k-space rows may be determined.

In a fifth act S25, it is determined whether a significant deviation exists between the corrected and the originally recorded k-space rows. For example, it may be determined whether the size of the deviation exceeds a predefined amount. The result of the comparison thus corresponds to a determination or decision whether the originally recorded k-space rows were or were not movement-impaired.

If this is the case ("Y"), the corrected k-space data is retained or the originally recorded k-space rows of the echo train are replaced by the corrected k-space rows in act S26.

However, if there is no significant deviation between the corrected and the originally recorded k-space rows ("N"), the originally recorded k-space rows are retained.

In act S27, a further echo train of the k-space is selected, and the acts S22 to S26 are performed afresh for the further echo train.

This procedure is continued until the acts S22 to S26 have been applied to the k-space rows of all echo trains of a TSE recording.

At least the acts S22 to S27 may be carried out by a correspondingly set up (e.g., programmed) data processing device D. The data processing device D may represent a part of an MR system, by which act S21 may also be carried out.

Figure 4:
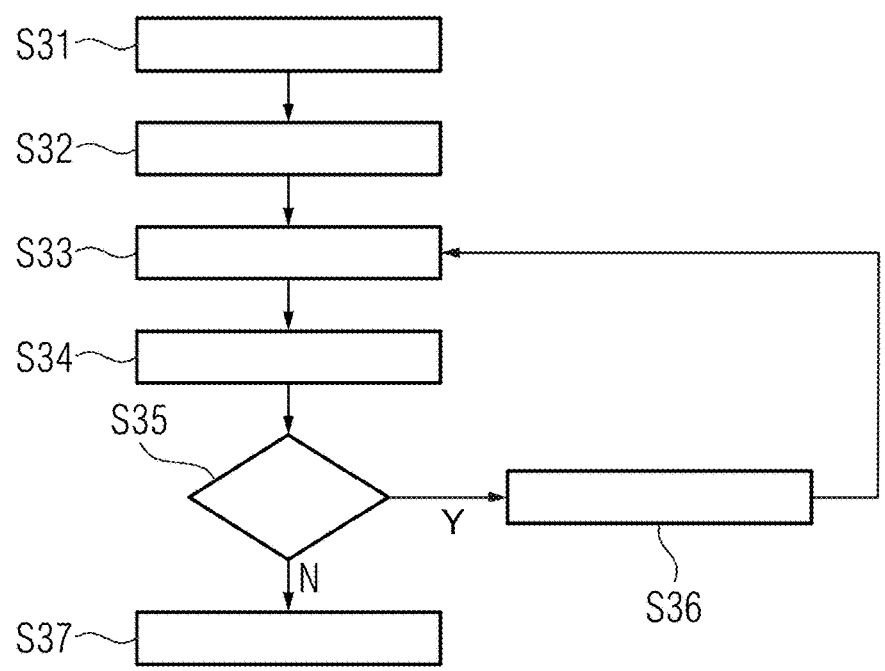
FIG. 4 shows a flow diagram of a third exemplary embodiment of the method.

FIG. 4 shows a flow diagram of a third exemplary embodiment of the method.

In a first act S31, a TSE recording of an MR object with multiple TSE sequences or echo trains is performed.

In a second act S32, a particular "first" echo train of the k-space is selected.

In a third act S33, the k-space rows pertaining to this echo train are replaced by k-space rows reconstructed by GRAPPA.

In a fourth act S34, a corresponding corrected MR image is generated from the thus generated "corrected" k-space and is saved.

In a fifth act S32, a check is made to see whether a further, as yet uncorrected echo train is present.

If the answer is yes ("Y"), a further, as yet uncorrected echo train is selected in act S36, and the acts S33 and S34 are applied to this echo train or the associated k-space.

If the answer is no ("N"), a final MR image is generated from the corrected MR images in act S37 (e.g., by pixel-by-pixel average value formation of corresponding pixels of all corrected MR images, etc.).

At least the acts S32 to S37 may be carried out by a correspondingly set up (e.g., programmed) data processing device D. The data processing device D may represent a part of an MR system, by which act S31 may also be carried out.

Although the invention has been illustrated and described in detail by the exemplary embodiments shown, the invention is not restricted thereto, and other variations may be derived therefrom by a person skilled in the art without departing from the protective scope of the invention.

In general, "a", "an", etc. may be understood as singular or plural, in particular in the sense of "at least one" or "one or more", etc., provided this is not explicitly excluded (e.g., by the expression "exactly one", etc.).

A numerical value may also include the given value as a typical tolerance range, provided this is not explicitly excluded.

The elements and features recited in the appended claims may be combined in different ways to produce new claims that likewise fall within the scope of the present invention. Thus, whereas the dependent claims appended below depend from only a single independent or dependent claim, it is to be understood that these dependent claims may, alternatively, be made to depend in the alternative from any preceding or following claim, whether independent or dependent. Such new combinations are to be understood as forming a part of the present specification.

While the present invention has been described above by reference to various embodiments, it should be understood that many changes and modifications can be made to the described embodiments. It is therefore intended that the foregoing description be regarded as illustrative rather than limiting, and that it be understood that all equivalents and/or combinations of embodiments are intended to be included in this description.

The invention claimed is:

1. A method for correcting magnetic resonance (MR) object movements, the method comprising:
performing a recording of an MR object with multiple echo trains;
correcting k-space data pertaining to an echo train of the multiple echo trains regarded as impaired by a movement of the MR object, the correcting comprising linking to corresponding k-space data reconstructed by a PPA method at least from k-space data of other echo trains of the multiple echo trains;
correcting the k-space data of only one echo train of the multiple echo trains from a k-space of all measured k-space data;
storing a corrected k-space that includes k-space data present after the correcting of the k-space data of only the one echo train;
repeating the correcting of the k-space data of only the one echo train and the storing for each echo train of the multiple echo trains; and
constructing an MR image from the corrected k-spaces.

2. The method of claim 1, wherein the recording is a TSE recording.

3. The method of claim 1, wherein the reconstructed k-space data is generated by a GRAPPA method.

4. The method of claim 3, wherein reconstructed k-space points of the reconstructed k-space data are generated by a 3×4 GRAPPA kernel.

5. The method of claim 1, wherein the linkage comprises a replacement of the k-space data pertaining to an impaired echo train by corresponding reconstructed k-space data.

6. The method of claim 1, wherein at least one movement-impaired echo train has been identified prior to the performance of the correction.

7. The method of claim 1, further comprising:
correcting corresponding original k-space data of the echo train;
determining a size of a deviation of the corrected k-space data of the echo train from the corresponding original k-space data;
retaining the corrected k-space data when the size of the deviation exceeds a predefined amount or retaining the original k-space data; and
repeating, for all echo trains of the number of echo trains, the correcting of the corresponding original k-space data of the echo train, the determining, and the retaining.

8. The method of claim 1, wherein storing the corrected k-space comprises generating an associated corrected MR image from the k-space and saving the associated corrected MR image, and
wherein constructing the MR image comprises generating a final MR image by overlaying the previously stored corrected MR images.

9. The method of claim 1, further comprising recording k-space data identified as or assumed to be movement-impaired afresh when a predefined condition is satisfied.

10. A data processing device comprising:
a processor configured to correct magnetic resonance (MR) object movements, the correction comprising:
performance of a recording of an MR object with multiple echo trains;
correction of k-space data pertaining to an echo train of the multiple echo trains regarded as impaired by a movement of the MR object, the correction comprising linkage to corresponding k-space data reconstructed by a PPA method at least from k-space data of other echo trains of the multiple echo trains;
correction of the k-space data of only one echo train of the multiple echo trains from a k-space of all measured k-space data;
storage of a corrected k-space that includes k-space data present after the correction of the k-space data of only the one echo train;
repetition of the correction of the k-space data of only the one echo train and the storage for each echo train of the multiple echo trains; and
construction of an MR image from the corrected k-spaces.

11. In a non-transitory computer-readable storage medium that stores instructions executable by one or more processors to correct magnetic resonance (MR) object movements, the instructions comprising:
performing a recording of an MR object with multiple echo trains;
correcting k-space data pertaining to an echo train of the multiple echo trains regarded as impaired by a movement of the MR object, the correcting comprising linking to corresponding k-space data reconstructed by a PPA method at least from k-space data of other echo trains of the multiple echo trains;
correcting the k-space data of only one echo train of the multiple echo trains from a k-space of all measured k-space data;
storing a corrected k-space that includes k-space data present after the correcting of the k-space data of only the one echo train;
repeating the correcting of the k-space data of only the one echo train and the storing for each echo train of the multiple echo trains; and
constructing an MR image from the corrected k-spaces.

* * * * *